(12) United States Patent
Meisberger et al.

(10) Patent No.: US 10,279,097 B2
(45) Date of Patent: May 7, 2019

(54) BLOOD PROCESSING APPARATUS COMPRISING A MEASUREMENT DEVICE

(71) Applicant: Fresenius Kabi Deutschland GmbH, Bad Homburg (DE)

(72) Inventors: Artur Meisberger, St. Wendel (DE); Melanie Fahrendorff, Troisdorf (DE); Ilka Sternheimer, Frankfurt (DE); Lars Michel, Rosbach v.d.H. (DE); Frank Schmidt, Schiffweiler (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 273 days.

(21) Appl. No.: 15/503,124

(22) PCT Filed: Aug. 3, 2015

(86) PCT No.: PCT/EP2015/067811
§ 371 (c)(1),
(2) Date: Feb. 10, 2017

(87) PCT Pub. No.: WO2016/030145
PCT Pub. Date: Mar. 3, 2016

(65) Prior Publication Data
US 2017/0232178 A1 Aug. 17, 2017

(30) Foreign Application Priority Data
Aug. 29, 2014 (EP) ..................... 14182874

(51) Int. Cl.
*A61M 1/36* (2006.01)
*A61M 1/02* (2006.01)
(Continued)

(52) U.S. Cl.
CPC ........ *A61M 1/3609* (2014.02); *A61M 1/0209* (2013.01); *A61M 1/0259* (2013.01);
(Continued)

(58) Field of Classification Search
CPC .............. A61M 1/0209; A61M 1/3609; A61M 1/0281; A61M 1/36; A61M 1/361;
(Continued)

(56) References Cited

U.S. PATENT DOCUMENTS 5,298,171 A * 3/1994 Biesel ................. A61M 1/3693
210/103
5,385,539 A 1/1995 Maynard
(Continued)

FOREIGN PATENT DOCUMENTS

| EP | 0358873 | 3/1990 |
| EP | 1287839 | 3/2003 |
| WO | WO2003/101510 | 12/2003 |

OTHER PUBLICATIONS

International Search Report and Written Opinion, counterpart PCT Appl. No. PCT/EP2015/067811, dated Oct. 8, 2015 (10 pages).

*Primary Examiner* — Leslie R Deak
(74) *Attorney, Agent, or Firm* — Cook Alex Ltd.

(57) ABSTRACT

A blood processing apparatus (1) comprises a measurement device (8) having a first chamber element (80) for measuring a haematocrit value of a blood fluid, the first chamber element (80) comprising a first inlet port (800) connectable to a first reservoir container (2) for allowing a flow from the first reservoir container (2) into the first chamber element (80) and a first outlet port (801) for allowing a flow out of the first chamber element (80), and the second chamber element (81) comprising a second inlet port (810) for allowing a flow into the second chamber element (81) and a second outlet port (811) connectable to a second reservoir container (3) for allowing a flow out of the second chamber element (81) towards the second reservoir container (3). The blood processing apparatus furthermore comprises a first pump mechanism (600) for pumping a blood fluid in a flow direction (F1) from the first reservoir container (2) towards
(Continued)

the blood processing apparatus (1), and a second pump mechanism (610) for pumping a blood fluid in a flow direction (F2) from the blood processing apparatus (1) towards the second reservoir container (2). Herein, the first pump mechanism (600) is located upstream of the first inlet port (800) of the first chamber element (80) and the second pump mechanism (610) is located upstream of the second inlet port (810) of the second chamber element (81). In this way a blood processing apparatus comprising a measurement device is provided which in an easy and reliable manner allows for a measurement of in particular a haematocrit value in the incoming blood flow as well as the outgoing blood flow.

11 Claims, 8 Drawing Sheets

(51) Int. Cl.
*G01N 33/49* (2006.01)
*G01N 29/02* (2006.01)

(52) U.S. Cl.
CPC ............ *A61M 1/0281* (2013.01); *A61M 1/36* (2013.01); *A61M 1/361* (2014.02); *A61M 1/3612* (2014.02); *A61M 1/3632* (2014.02); *A61M 1/3692* (2014.02); *A61M 1/3693* (2013.01); *G01N 29/02* (2013.01); *G01N 33/49* (2013.01); *G01N 33/4915* (2013.01); *A61M 2205/12* (2013.01); *A61M 2205/121* (2013.01); *A61M 2205/3375* (2013.01); *A61M 2209/086* (2013.01); *A61M 2230/207* (2013.01); *G01N 2291/02466* (2013.01)

(58) Field of Classification Search
CPC .............. A61M 1/3612; A61M 1/3692; A61M 1/3693; A61M 2230/207; G01N 2291/02466; G01N 33/49
See application file for complete search history.

(56) References Cited

U.S. PATENT DOCUMENTS

| | | | |
|---|---|---|---|
| 5,876,611 A * | 3/1999 | Shettigar | A61M 1/3621 210/103 |
| 2003/0042181 A1 | 3/2003 | Metzner | |
| 2003/0138349 A1 | 7/2003 | Robinson et al. | |
| 2003/0222029 A1* | 12/2003 | Muller | A61M 1/3693 210/739 |
| 2005/0230292 A1 | 10/2005 | Beden et al. | |
| 2009/0211987 A1 | 8/2009 | Min | |

* cited by examiner

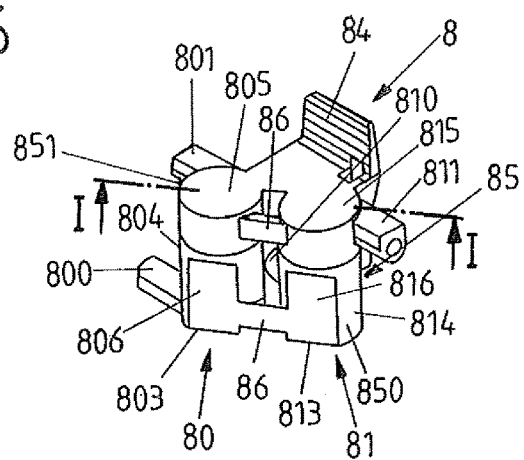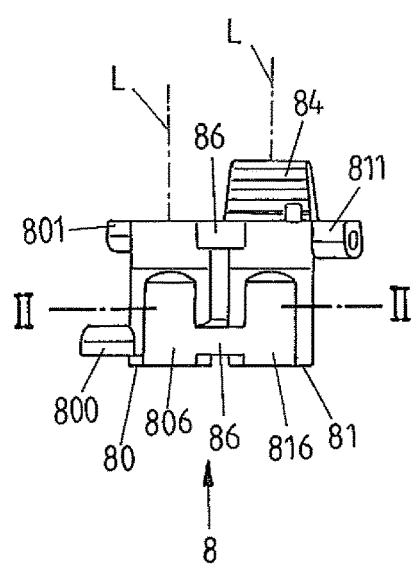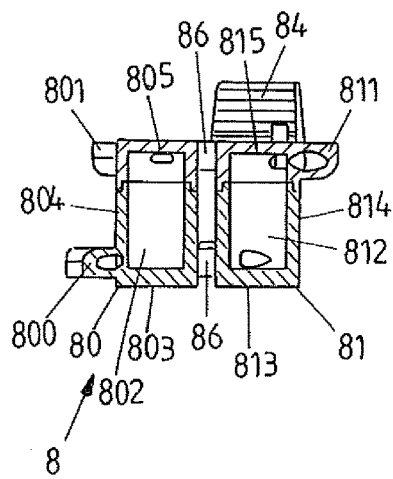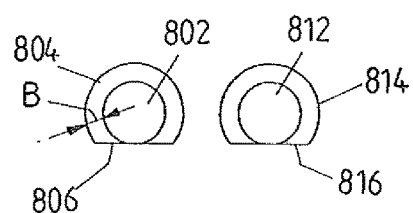

BLOOD PROCESSING APPARATUS COMPRISING A MEASUREMENT DEVICE

The present application is a U.S. National Stage of PCT International Patent Application No. PCT/EP2015/067811, filed Aug. 3, 2015, which claims priority to EP Application No. 14182874.9, filed Aug. 29, 2014, both of which are hereby incorporated herein by reference.

The invention relates to a blood processing apparatus according to the preamble of claim 1.

A blood processing apparatus of this kind comprise a measurement device having a first chamber element for measuring a haematocrit value of a blood fluid, the first chamber element comprising a first inlet port connectable to a first reservoir container for allowing a flow from the first reservoir container into the first chamber element, and a first outlet port for allowing a flow out of the first chamber element.

In addition, the measurement device comprises a second chamber element comprising a second inlet port for allowing a flow into the second chamber element and a second outlet port connectable to a second reservoir container for allowing a flow out of the second chamber element towards the second reservoir container.

The blood processing apparatus may for example be constituted as an autotransfusion system in which blood collected from a patient during or after a surgical operation is processed and recycled for re-transfusing it into the patient. In this case, the first reservoir container may be a container for collecting blood from the patient during or after surgery, whereas the second reservoir container may be a container for collecting processed blood for re-transfusing it into the patient. From the first reservoir container the blood is delivered through the first chamber element to for example a washing chamber of the autotransfusion system, where it is processed and, after processing, delivered through the second chamber element to the second reservoir container.

By means of the measurement device comprising the first chamber element and the second chamber element hence a haematocrit value of blood flowing into the blood processing apparatus as well as a haematocrit value of (processed) blood flowing out of the blood processing apparatus may be measured.

To deliver blood from the first reservoir container towards the blood processing apparatus through the first chamber element a first pump mechanism is provided. To vice versa deliver blood from the blood processing apparatus towards the second reservoir container through the second chamber element a second pump mechanism is provided.

EP 1 287 839 B1 discloses a measurement device comprising a disposable cassette. The disposable cassette is received in a reception chamber of a dialysis apparatus and includes a chamber having an inlet port and an outlet port. A temperature sensor is arranged on the chamber for measuring the temperature of blood contained in the chamber. An ultrasonic transmitter and an ultrasonic transceiver are arranged on opposite sides of the chamber for ultrasonically measuring a haematocrit value of blood contained in the chamber.

EP 0 358 873 B1 discloses an extracorporeal blood circuit of a dialysis machine in which in a blood conduit upstream of the dialysis machine a temperature measurement device and an ultrasonic sensor are arranged.

It is an object of the instant invention to provide a blood processing apparatus comprising a measurement device which in an easy and reliable manner allows for a measurement of in particular a haematocrit value in the incoming blood as well as the outgoing blood.

This object is achieved by means of a blood processing apparatus comprising the features of claim 1.

Accordingly, the first pump mechanism is located upstream of the first inlet port of the first chamber element and the second pump mechanism is located upstream of the second inlet port of the second chamber element.

This is based on the idea to locate the first pump mechanism and the second mechanism upstream of the respective chamber elements such that by means of each pump mechanism a blood fluid is pumped through the associated chamber element downstream of the respective pump mechanism.

Namely, the first pump mechanism is located upstream of the first chamber element such that the first chamber element is arranged on the pressure side of the first pump mechanism.

Analogously, the second pump mechanism is located upstream of the second chamber element such that the second element is located on the pressure side of the second pump mechanism.

Because the chamber elements each are located on the pressure side of the respective associated pump mechanism, a generation of gas bubbles through cavitation at the chamber elements is reduced to a minimum. Such cavitation effects may predominantly occur on the suction side of the pump mechanisms due to a negative pressure being generated at the suction side, but are less likely to occur on the pressure side downstream the pump mechanism.

Because the risk for bubbles occurring in the chamber elements is reduced, parameters of the blood flowing through the chamber elements may be determined in a reliable manner without the presence of gas, in particular air bubbles disturbing the measurement. In particular, a haematocrit value of blood flowing through the chamber elements may be determined.

The blood processing apparatus in particular may be an autotransfusion system for collecting blood from a patient during or after a surgical operation, for processing and recycling it, and for re-transfusing it to the patient. By measuring the haematocrit of the blood entering the blood processing apparatus as well as of the blood exiting the blood processing apparatus a beneficial control of operation of the blood processing apparatus becomes possible. In particular, by measuring the haematocrit of the incoming blood processing parameters may be set in order to obtain a desired haematocrit after processing. By reading the haematocrit of the outgoing (processed) blood, a feedback may be obtained which again may be used for controlling the processing procedure (compare for example the European patent application with application number 14152634.3).

The blood processing apparatus, in one embodiment, comprises a holder device for holding the measurement device. The holder device comprises a base having a reception opening for receiving the measurement device and a closure element movably arranged on the base for locking the measurement device in an inserted position in the reception opening.

The holder device beneficially comprises a first ultrasonic sensor element which in the inserted position of the measurement device faces the bottom wall of the first chamber element and a second ultrasonic sensor element which in the inserted position of the measurement device faces the bottom wall of the second chamber element. The holder device hence is adapted to conduct measurements of haematocrit in the two chamber elements.

In addition, the holder device may comprise a first infrared sensor element which in the inserted position of the measurement device faces a circumferential wall of the first chamber element and a second infrared sensor element which in the inserted position of the measurement device faces a circumferential wall of the second chamber element. The holder device hence comprises two infrared sensor elements for measuring the temperature in the two chamber elements.

For receiving the measurement device, the base may for example comprise a first tilted face and a second tilted face extending transversely with respect to the first tilted face. The first tilted face and the second tilted face hence describe a right angle with respect to each other. Herein, the ultrasonic sensor elements are arranged on the first tilted face, whereas the infrared sensor elements are arranged on the second tilted face. In the inserted position of the measurement device the bottom walls of the chamber elements face the first tilted face, whereas the circumferential walls face the second tilted face such that the ultrasonic sensor elements come to lie at the bottom walls and the infrared sensor elements come to lie at the circumferential walls of the chamber elements.

The first inlet port of the first chamber element is connectable to the first reservoir container, for example a container for collecting blood of a patient during or after a surgical operation. The first outlet port of the first chamber element may in turn for example be connected to a washing chamber of the blood processing apparatus for allowing a flow of blood into the washing chamber. The washing chamber may be rotatably arranged in a housing of the blood processing apparatus and may be constituted to conduct a separation of blood into its various constituents by performing a centrifugation. Through the first chamber element, hence, a blood flow into the washing chamber is provided.

The second inlet port of the second chamber element, in turn, may be connected to the washing chamber for receiving a flow of (processed) blood from the washing chamber. The second outlet port of the second chamber element is connectable to a second reservoir container, for example a bag for collecting the processed blood for re-transfusing it to the patient, such that through the second chamber element the outgoing processed blood flows from the washing chamber towards the second reservoir container.

The first pump mechanism and the second pump mechanism may, for example, be constituted as peristaltic pumps acting on tube segments of a tubing set. For example, the first pump mechanism may act on a first tube segment connected to the first inlet port of the first chamber element, whereas the second chamber element acts on a second tube segment connected to the second inlet port of the second chamber element. The first pump mechanism and the second pump mechanism, thus, both are arranged upstream of the associated, respective chamber element and act on tube segments upstream of the respective chamber element.

The measurement device may, for example, be part of a tubing set. A first inlet-side tube section of the tubing set may be connected to the first inlet port of the first chamber element, and a first outlet-side tube section may be connected to the first outlet port of the first chamber element. A second inlet-side tube section may be connected to the second inlet port of the second chamber element, and a second outlet-side tube section may be connected to the second outlet port of the second chamber element. The tubing set may comprise further tube sections and in particular may also comprise tube segments onto which the pump mechanisms are adapted to act.

The tubing set may be connected to a washing chamber which may be disposable together with the tubing set.

The first and the second chamber element, in one embodiment, each may have a generally cylindrical shape and may extend along a longitudinal axis. Each chamber element comprises a circumferential wall extending about the longitudinal axis and encompassing a flow chamber contained in the chamber element. The first and the second chamber element herein may, with their respective longitudinal axis, extend in parallel to each other such that the chamber elements are arranged side by side.

Herein, the first and the second chamber element may integrally be connected to form an integral unit. For connecting the first and the second chamber element to each other, webs may extend in-between the first and the second chamber element such that a distance in-between the first and the second chamber element is provided allowing for independent measurements in the chamber elements, i.e., without a blood stream through the first chamber element affecting a blood stream through the second chamber element and vice versa.

The idea underlying the invention shall subsequently be described in more detail with regard to the embodiments shown in the figures. Herein:

FIG. 6 shows a perspective view of an embodiment of a measurement device comprising two chamber elements;

FIG. 7A shows a side view of the measurement device according to FIG. 6;

FIG. 7B shows a sectional view of the measurement device along the line I-I according to FIG. 6;

FIG. 7C shows a sectional view of the measurement device along the line II-II according to FIG. 7A;

FIG. 1 shows a blood processing apparatus 1 which may be constituted for example as a so-called continuous autotransfusion system (CATS).

An autotransfusion system may serve to collect blood from a patient for example during or after a surgical operation. The collected blood is processed within the autotransfusion system and is recycled in order to re-transfuse it into the patient.

Figure 1:
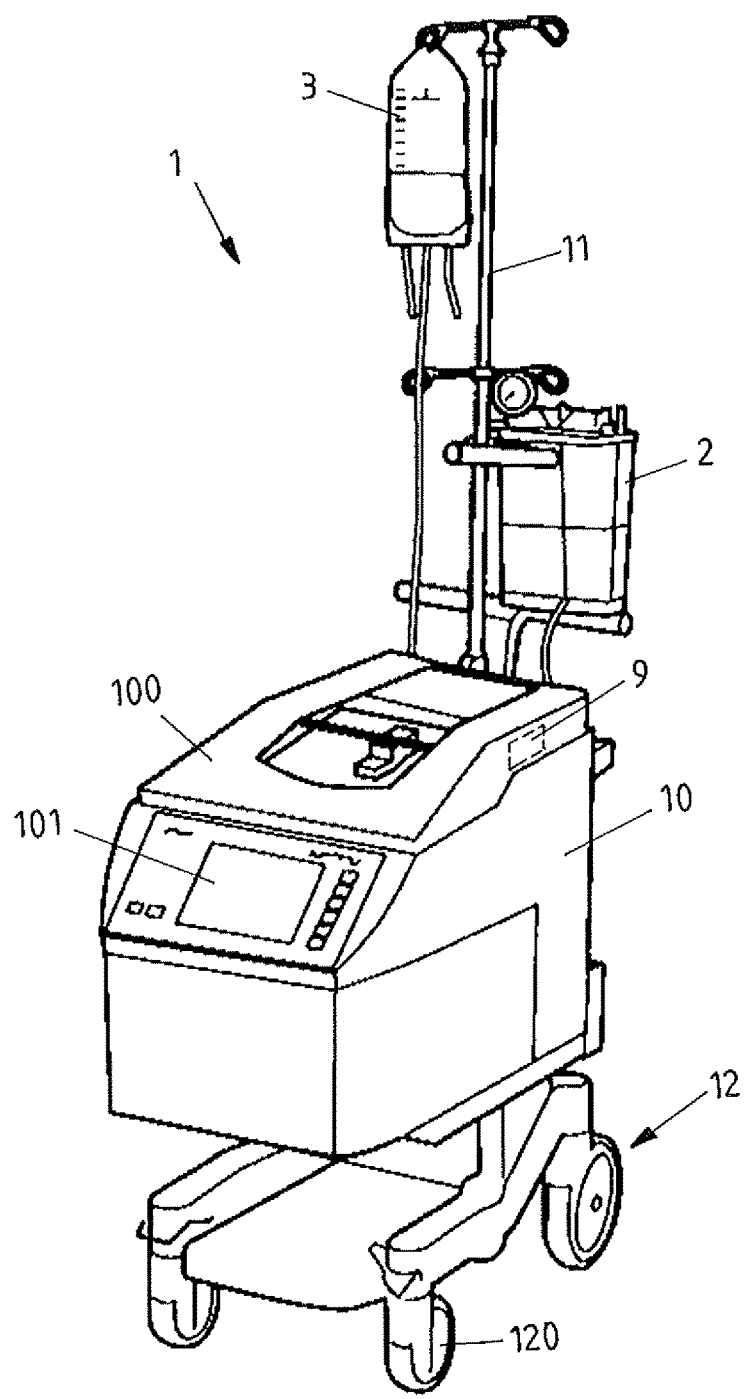
FIG. 1 shows a blood processing apparatus.

The blood processing apparatus 1 of FIG. 1 constituting an autotransfusion system for this purpose comprises a first reservoir container 2 for collecting blood from a patient. Through a tubing set the blood is guided from the reservoir container 2 to a washing chamber 7 (see FIGS. 2 and 3) contained in a housing 10 of the blood processing apparatus 1, by means of which the blood is processed and, after processing, collected in a second reservoir container 3 constituting a so-called re-transfusion bag, from which the blood may be re-transfused to the patient.

In the example of FIG. 1, the housing 10 comprises a lid 100 which may be opened in order to access the washing chamber 7 contained in the housing 10 and to arrange the tubing set within the housing 10 in a suitable manner. The housing 10 furthermore comprises a control panel 101 via which control commands for operating the blood processing apparatus 1 may be entered.

The housing 10 is arranged on a base 12 comprising wheels 120 such that the blood processing apparatus 1 is mobile for example in an operating theatre of a hospital.

From the housing 10 a stand 11 extends vertically on which the first reservoir container 2 for collecting the patient's blood and a second reservoir container 3 for collecting the processed blood for re-transfusing it to the patient are arranged.

On the stand 11 further containers, such as a bag for a washing solution 4 (see FIGS. 2 and 3), may be arranged.

Figure 2:
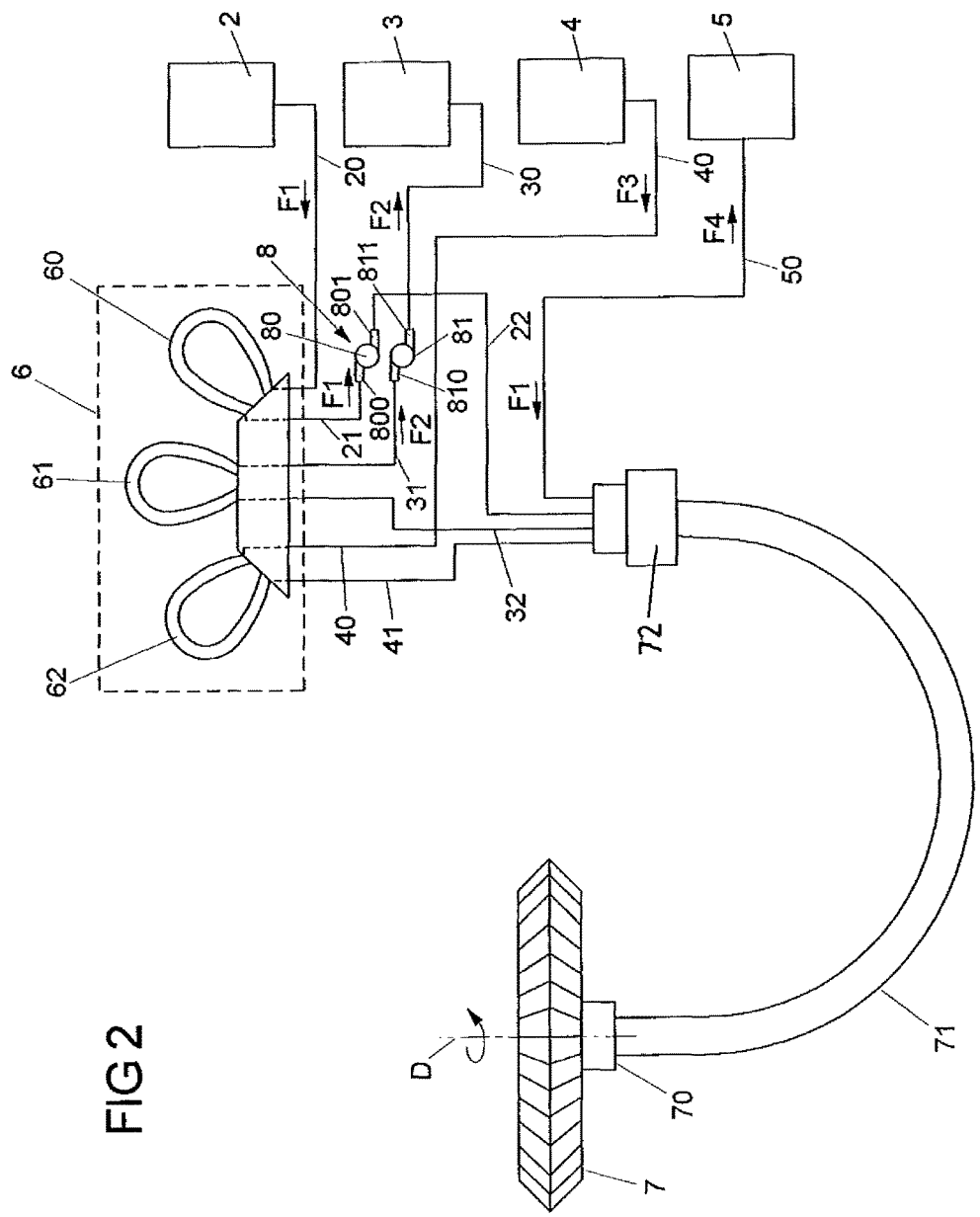
FIG. 2 shows a schematic drawing of a tubing set used with a blood processing apparatus.
Figure 3:
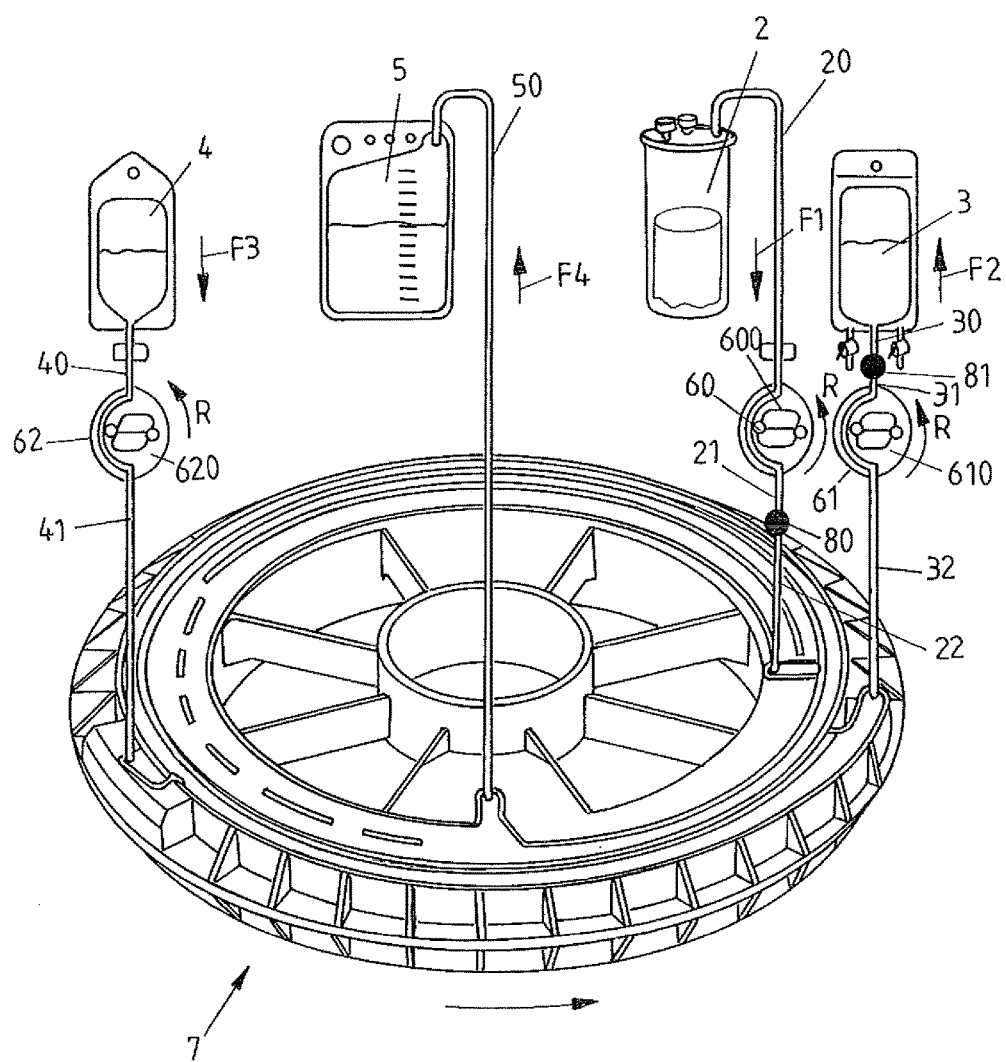
FIG. 3 shows a schematic drawing of the tubing set in relation to a washing chamber of the blood processing apparatus.

The functional setup of the blood processing apparatus 1 is as shown in FIGS. 2 and 3.

The washing chamber 7 contained in the housing 10 is rotatable about a rotational axis D and, during operation of the blood processing apparatus 1, is rotated about the rotational axis D in order to perform a centrifugation process within the washing chamber 7. The washing chamber 7 comprises a connector 70 from which a conduit 71 extends towards another connector 72.

As functionally shown in FIG. 3, the first reservoir container 2 containing blood collected from the patient, the second reservoir container 3 constituting a re-transfusion bag for re-transfusing blood to the patient, a bag for a washing solution 4, in particular a saline solution, and a waste bag 5 via a tubing set comprising different tube sections are connected to the washing chamber 7. The different tube sections herein are effectively connected at different locations on the washing chamber 7, as shown in FIG. 3.

As shown in FIG. 3, the first reservoir container 2 via a tube section 20 is connected to a tube segment 60 on which a peristaltic pump mechanism 600 acts. By means of the pump mechanism 600 a flow from the reservoir container 2 is caused through a tube section 21 via a chamber element 81 of a measurement device 8 and a tube section 22 towards the washing chamber 7.

The second reservoir container 3 is connected via a tube section 30 to a chamber element 81 of the measurement device 8 and via a tube section 31 to a tube segment 61 on which a second peristaltic pump mechanism 610 acts. The tube segment 61 via a tube section 32 is connected to the washing chamber 7.

The bag of the washing solution 4 is connected via a tube section 40 to a tube segment 62 on which a third peristaltic pump mechanism 620 acts. The tube segment 62 is connected via a tube section 41 to the washing chamber 7.

The pump mechanisms 600, 610, 620 each are constituted to perform a peristaltic pump action. For this, each pump mechanism 600, 610, 620 during operation of the blood processing apparatus 1 performs a rotational movement R and through this rotational movement R acts on the respective tube segment 60, 61, 62.

The pump mechanism 600 acting on the tube segment 60 connected to the first reservoir container 2 and likewise the pump mechanism 620 acting on the tube segment 62 connected to the bag for the washing solution 4 cause a flow in a flow direction F1, F3 towards the washing chamber 7 such that blood from the first reservoir container 2 and a washing solution from the bag 4 are transported towards the washing chamber 7.

The pump mechanism 610 acting on the tube segment 61 connected to the second reservoir container 3 for collecting processed blood for re-transfusing it to the patient, in contrast, causes a flow in a flow direction F2 from the washing chamber 7 towards the second reservoir container 3.

The waste bag 5 is connected via a tube section 50 directly to the washing chamber 7, without a pump mechanism acting on the tube section 50. During operation of the blood processing apparatus 1 a flow in a flow direction F4 from the washing chamber 7 towards the waste bag 5 is caused.

As schematically shown in FIG. 2, the tube segments 60, 61, 62, on which the three pump mechanisms 600, 610, 620 act, are arranged in a pump bed 6 in a manner known per se.

During operation of the blood processing apparatus 1 blood is transported from the reservoir container 2 into the washing chamber 7 and is processed within the washing chamber 7 in order to recycle and collect it for re-transfusion in the reservoir container 3. The processing herein takes place in the washing chamber 7 in different phases.

In a first phase—the so-called first separation phase—blood enters from the reservoir container 2 into the washing chamber 7 by pumping action of the pump mechanism 600 delivering the blood through the tube sections 20-22. In this initial separation stage, the blood is concentrated to a haematocrit value of approximately 80% within the washing chamber 7, and most of the blood plasma, cellular debris, white blood cells, platelets, anti-coagulant and other unwanted constituents are separated out and flow through the tube section 50 into the waste bag 5. This separation is effected by the rotary movement of the washing chamber 7 causing a centrifugation and, hence, a separation of the blood into its different components.

During a second phase—the so-called washing phase—the remaining constituents of the blood, in particular red blood cells, are re-suspended with a washing solution, for example a saline solution delivered from the bag for the washing solution 4 through tube sections 40, 41 by the pumping action of the pump mechanism 620. In the washing phase also a further removal of blood plasma occurs.

In a third phase—the so-called second separation phase—a final separation takes place. In this phase, the red blood cells are packed to a haematocrit value concentration of about 60 to 65%. During this phase the saline solution added during the washing phase is again removed.

The blood processed in this way leaves the washing chamber 7 through tube sections 32, 31, 30 and, by means of the pumping action of the pump mechanism 610, is pumped into the reservoir container 3 where it is collected for re-transfusion into the patient.

As shown in FIG. 2, a measurement device 8 is placed within the tubing set. The measurement device 8 serves to determine the haematocrit value in the blood flowing from the reservoir container 2 towards the washing chamber 7 and in the blood exiting the washing chamber 7 and flowing towards the reservoir container 3 for collecting the processed blood for re-transfusion. The measurement device 8 comprises two chamber elements 80, 81, each having an inlet port 800, 810 and an outlet port 801, 811.

The reservoir container 2 via its tube sections 20, 21 is connected to the inlet port 800 of the first chamber element 80, whereas the outlet port 801 of the first chamber element 80 is connected via the tube section 2 to the washing chamber 7. The washing chamber 7 in turn is connected via the tube sections 32, 31 to the inlet port 810 of the second chamber element 81, wherein the outlet port 811 of the second chamber element 81 via the tube section 30 is connected to the reservoir container 3.

As depicted in FIG. 3, the chamber elements 80, 81 of the measurement device 8 in each case are arranged downstream from the respective pump mechanism 600, 610. In particular, the pump mechanism 600 causing the flow from the reservoir container 2 towards the washing chamber 7 is arranged upstream of the inlet port 800 of the first chamber element 80. The pump mechanism 610 for delivering the processed blood into the reservoir container 3 for re-transfusing the processed blood into the patient is arranged upstream of the inlet port 810 of the second chamber element 81.

Because the chamber elements 80, 81 each are arranged downstream from the pump mechanism 600, 610, each chamber element 80, 81 is arranged on the pressure side of the respective pump mechanism 600, 610. This has the beneficial effect that cavitation effects, as they may occur upstream the pump mechanism 600, 610 due to a negative pressure created upstream by suction of the pump mechanism 600, 610, can be reduced to a minimum such that such cavitation effects do not impact measurements within the chamber elements 80, 81.

The measurement device 8 with its chamber elements 80, 81 serves to measure the haematocrit value of the blood flowing from the reservoir container 2 into the washing chamber 7 and from the washing chamber 7 into the reservoir container 3. Measuring the haematocrit value within the blood flowing from the reservoir container 2 towards the washing chamber 7 allows for controlling the process dependent on the haematocrit of the blood streaming into the washing chamber 7. Measuring the haematocrit in the processed blood flowing from the washing chamber 7 towards the reservoir container 3 provides information about the processed blood and the haematocrit obtained therein and allows for an adjustment of process parameters to obtain a desired haematocrit value.

Figure 4:
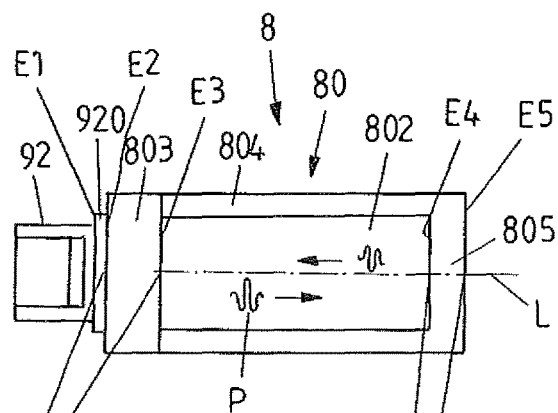
FIG. 4 shows a schematic view of a chamber element of a measurement device.
Figure 5:
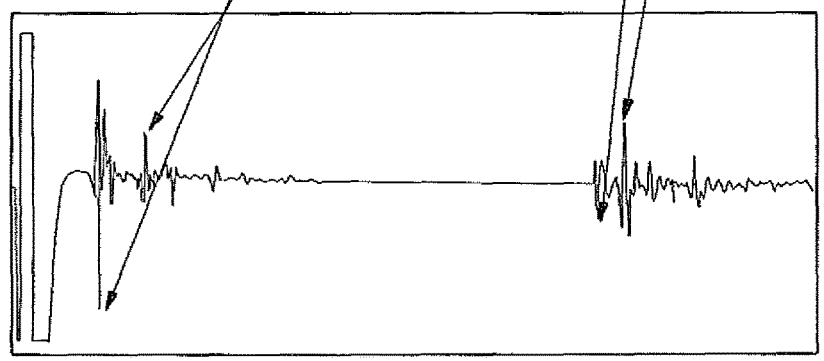
FIG. 5 shows a sensor signal received at a sensor element for measuring a haematocrit value of a blood fluid contained in the chamber element.

The measurement device 8 with its chamber elements 80, 81, as mentioned, serves to measure the haematocrit value of blood flowing through the chamber elements 80, 81. The measurement herein is carried out, as shown in FIGS. 4 and 5, by transmitting ultrasonic pulses P from an ultrasonic sensor element 92 into an associated chamber element 80, 81 and by receiving reflection signals occurring within the chamber element 80, 81. By examining the propagation times of pulses P within the chamber element 80, 81, the density of the blood contained in the chamber element 80, 81 can be analyzed and the haematocrit of the blood can be derived.

As shown in FIG. 6 and FIG. 7A to 7C, each chamber element 80, 81 has a generally cylindrical shape. Each chamber element 80, 81 comprises a bottom wall 803, 813, a circumferential wall 804, 814 and a top wall 805, 815. The bottom wall 803, 813, the circumferential wall 804, 814 and the top wall 805, 815 together define a flow chamber 802, 812 through which the blood flows.

Returning to FIG. 4, an ultrasonic sensor element 92 is arranged on the bottom wall 803 of the chamber element 80 and is coupled to the bottom wall 803 via a coupling pad 920. The ultrasonic sensor element 92 is constituted to emit ultrasonic pulses P generally along a longitudinal axis L along which the chamber element 80 with its flow chamber 802 contained therein extends.

As shown in the curve of FIG. 5, when emitting an ultrasonic pulse P into the chamber element 80, reflections occur at different faces E1-E5 of the chamber element 80.

In particular, a first reflection occurs at a face E2 in-between the coupling pad 920 and the bottom wall 803. A second reflection occurs at the face E3 of the bottom wall 803 towards the flow chamber 802. A third reflection occurs at the face E4 of the top wall 805 towards the flow chamber 802. And a fourth reflection occurs at the face E5 of the top wall 805 towards the outside.

Such reflections may be recorded in the ultrasonic sensor element 92, and from the recorded reflections the propagation times may be measured. If the geometry of the chamber element 80 is known, the densities of the materials through which the pulse P has propagated can be concluded. From the density of the blood in the flow chamber 802, then, the haematocrit value of the blood contained in the flow chamber 802 can be derived.

In order to calibrate the measurement device 8, an initial measurement may be taken by using a saline solution having a known density in order to derive the length of the different paths of the chamber element 80.

The length of the different paths in the chamber element 80 should be chosen such that reflections at the different faces E1-E5 can be discerned in a reliable manner. For this, the thickness of the bottom wall 803 and the top wall 805 and the length of the flow chamber 802 along the longitudinal axis L should be chosen appropriately.

The coupling pad 920 serves to obtain a beneficial coupling of the sensor element 92 to the bottom wall 803 of the chamber element 80. As will be described later, it may be suitable to press the chamber element 80 with its bottom wall 803 against the coupling pad 920 with a suitable force (for example exceeding 15 N).

FIGS. 6 and 7A, 7B show an embodiment of a measurement device 8 comprising two chamber elements 80, 81 integrally connected to each other via webs 86 to form an integral measurement unit. The measurement device 8 herein is fabricated from two housing parts 850, 851 to form a housing 85. The housing parts 850, 851 may be separately fabricated for example by injection molding from a plastics material, for example a polymer such as polycarbonate, and may subsequently be joined together to form the measurement device 8.

Each chamber element 80, 81 extends longitudinally along a longitudinal axis L. The longitudinal axes L of the chamber elements 80, 81 herein extend in parallel with respect to each other. Each chamber element 80, 81 comprises a circumferential wall 804, 814 circumferentially extending about the respective longitudinal axis L such that two generally cylindrical chamber elements 80, 81 are formed.

Each chamber element 80, 81 comprises an inlet port 800, 810 and an outlet port 801, 811. The inlet port 800, 810, in each case, is arranged in the vicinity of the bottom wall 803, 813, whereas the outlet port 801, 811 in each case is arranged in the vicinity of the top wall 805, 815.

As shown in FIG. 7B, the inlet ports 800, 810 open into the respective flow chamber 802, 812 immediately inside the bottom wall 803, 813, whereas the outlet ports 801, 811 open into the respective flow chamber immediately inside the top wall 805, 815.

As shown in FIG. 7A, the inlet port 800, 810 and the outlet port 801, 811 for each chamber element 80, 81 are arranged on the circumferential wall 804, 814 of the respective chamber element 80, 81 and are displaced with respect to each other along the longitudinal axis L. The inlet port 800, 810 and the outlet port 801, 811 hence are arranged at different heights with respect to the longitudinal axis L.

Figure 8A:
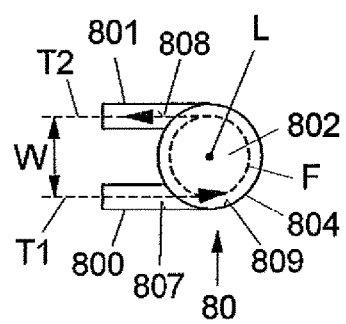
FIG. 8A shows a schematic top view of a first chamber element of the measurement device.
Figure 8B:
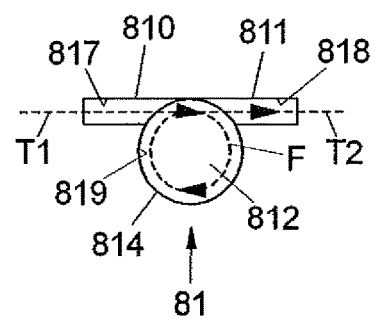
FIG. 8B shows a schematic top view of a second chamber element of the measurement device.

Furthermore, as schematically illustrated in FIG. 8A for the first chamber element 80 and in FIG. 8B for the second chamber element 81, the inlet port 800, 810 and the outlet port 801, 811 each comprise a conduit 807, 808, 817, 818 for allowing a flow into the flow chamber 802, 812 respectively out of the flow chamber 802, 812. The conduits 807, 808, 817, 818 extend along tangential axes T1, T2 which do not intersect with the longitudinal axis L and hence form skew lines with the longitudinal axis L.

In particular, the conduit 807 of the inlet port 800 of the first chamber element 80 extends along a first tangential axis T1 not intersecting with the longitudinal axis L, as shown in FIG. 8A. Likewise, the conduit 808 of the outlet port 801 of the first chamber element 80 extends along a second tangential axis T2, which runs in parallel to the first tangential axis T1 and is displaced by a displacement W from the first tangential axis T1.

For the first chamber element 80, blood flows into the flow chamber 802 in a first direction and leaves the flow chamber 802 through the outlet port 801 in an opposite, second direction. Due to the conduits 807, 808 extending along the tangential directions T1, T2, the inlet port 800 and the outlet port 801 open tangentially into the flow chamber 802 such that the flow F enters the flow chamber 802 tangentially with respect to an inner surface 809 of the flow chamber 802 and, likewise, tangentially exits the flow chamber 802 through the outlet port 801.

In combination with the displacement of the inlet port 800 and the outlet port 801 along the longitudinal axis L, this causes a turbulent flow F within the flow chamber 802, as it is illustrated in FIG. 8A. Such turbulent flow F reduces the risk for depositions within the flow chamber 802.

As shown in FIG. 8B for the second chamber element 81, the conduits 817, 818 of the inlet port 810 and the outlet port 811 of the second chamber element 81 likewise open tangentially into the flow chamber 812 to cause a turbulent flow F in the flow chamber 812. Herein, the tangential axes T1, T2 are in line with each other (when viewed from the top), but the inlet port 810 and the outlet port 811 extend towards different sides from the circumferential wall 814 of the second chamber element 81.

Figure 8C:
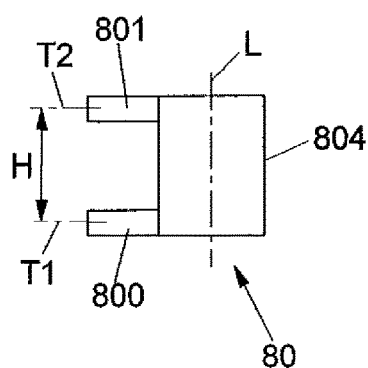
FIG. 8C shows a schematic side view of the first chamber element of the measurement device.
Figure 8D:
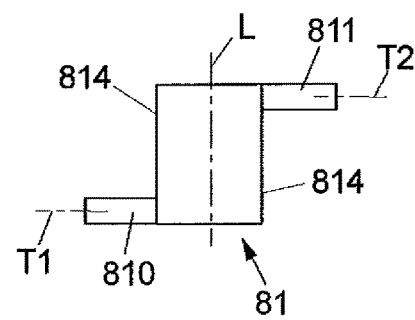
FIG. 8D shows a schematic side view of the second chamber element of the measurement device.

FIGS. 8C and 8D illustrate the longitudinal displacement of the inlet port 800, 810 and the outlet port 801, 811 for the different chamber elements 80, 81 along the respective longitudinal axis L. For both chamber elements 80, 81 the tangential axes T1, T2 along which the inlet port 800, 810 and the outlet port 801, 811 extend are displaced with respect to each other by a displacement H.

As visible from FIGS. 6 and 7A, each chamber element 80, 81 at the outside of its circumferential wall 804, 814 comprises a flat face 806, 816, the flat faces 806, 816 being aligned such that they lie in the same plane. As visible from the sectional drawing of FIG. 7C, in the region of the flat face 806, 816 the circumferential wall 804, 814 comprises a reduced wall thickness B.

The flat face 806, 816 of each chamber element 80, 81 serves for interaction with an infrared sensor element, as will be described later. Via the flat face 806, 816 the temperature inside the flow chamber 802, 812 may be measured by receiving infrared radiation emitted from the flat face 806, 816.

The measurement device 8 comprises a handle 84 for manually grabbing the measurement device 8. The handle 84 is arranged on the housing part 851 forming the top walls 805, 815 of the chamber elements 80, 81.

The measurement device 8 is part of the tubing set formed by the tube sections connecting the reservoir container 2, the reservoir container 3, the bag for the washing solution 4 and the waste bag 5 to the washing chamber 7. In particular, an autotransfusion set may be disposable and may consist of the washing chamber 7 and all tube sections for connecting the washing chamber 7 with the respective bags or containers 2-5, including the tube segments 60-62 interacting with the pump mechanisms 600-620.

The blood processing apparatus 1, as schematically shown in FIG. 1, receives in its housing 10 the washing chamber 7 and comprises a holder device 9 for receiving the measurement device 8. An embodiment of such a holder device 9 is shown in FIGS. 9 to 11.

Figure 9:
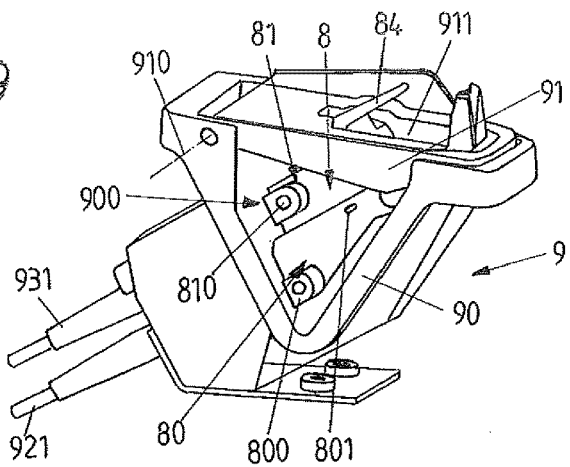
FIG. 9 shows a perspective view of a holder device of the blood processing apparatus with a measurement device received therein.
Figure 10:
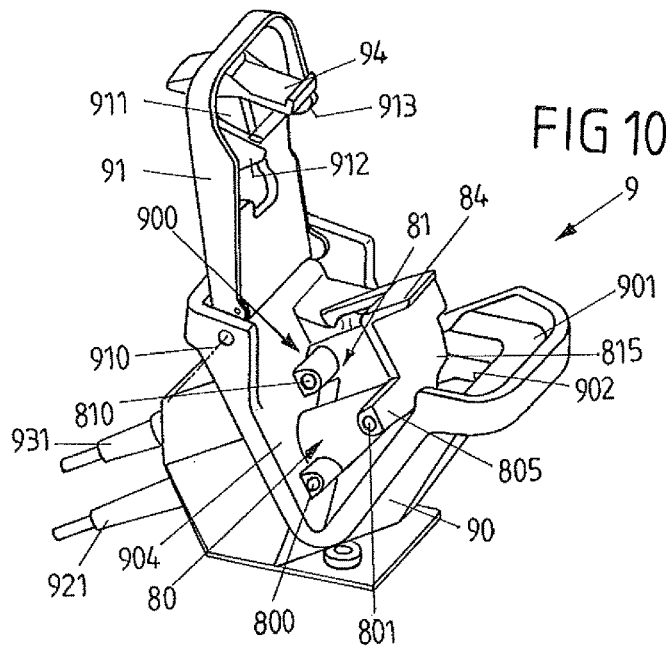
FIG. 10 shows a perspective view of the holder device with a closure element in an opened position.
Figure 11:
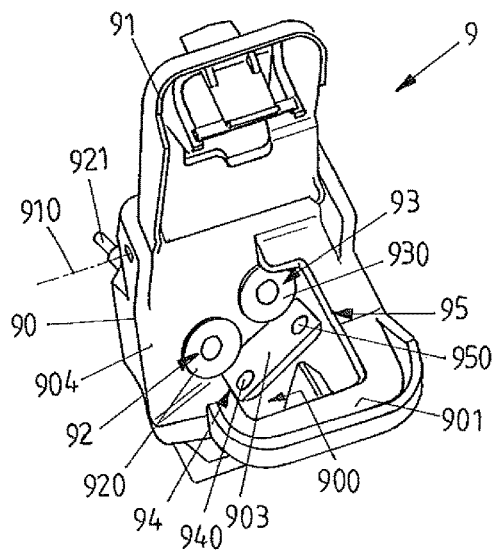
FIG. 11 shows a perspective view of the holder device, without a measurement device received therein.

The holder device 9 in the embodiment of FIGS. 9 to 11 comprises a base 90 and a closure element 91 which is arranged on the base 90 and is pivotable about a pivoting axis 910 with respect to the base 90. The base 90 forms a reception opening 900 into which the measurement device 8 with its chamber elements 80, 81 may be inserted such that, in an inserted position shown in FIGS. 9 and 10, the measurement device 8 is received in the reception opening 900.

Figure 12:
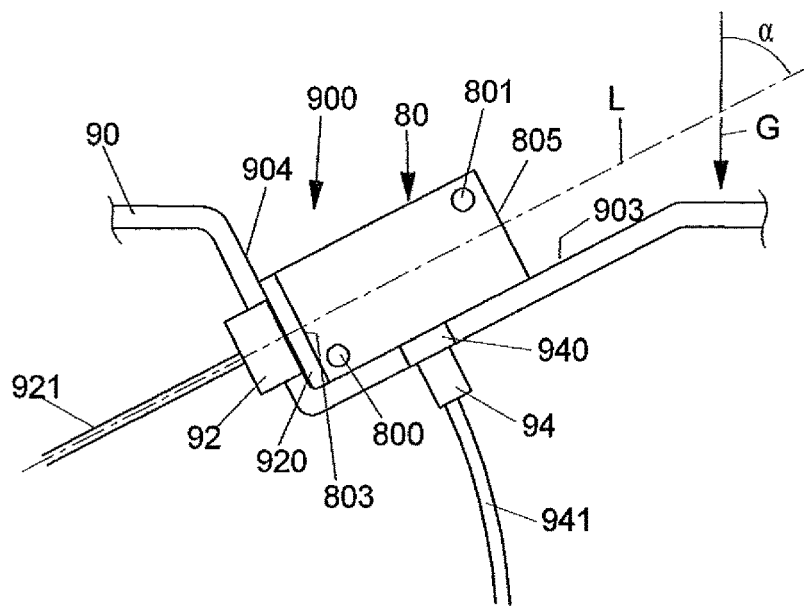
FIG. 12 shows a schematic view of the holder device in relation to a measurement device.

The base 90 comprises, as shown in FIG. 11 and as schematically illustrated in FIG. 12, a first tilted face 904 and a second tilted face 903. The tilted faces 903, 904 are arranged perpendicularly to each other and serve to abut the bottom walls 803, 813 respectively flat faces 806, 816 of the circumferential walls 804, 814 of the chamber elements 80, 81.

Herein, at the first tilted face 904 two ultrasonic sensor elements 92, 93 are arranged which comprise coupling pads 920, 930 and face with their coupling pads 920, 930 towards the outside. At the second tilted face 903 two infrared windows 940, 950 are arranged which are (at least partially) transparent for infrared radiation and form windows for infrared sensors 94, 95 located behind the infrared windows 940, 950, as schematically shown in FIG. 12.

In its inserted position the measurement device 8 with its chamber elements 80, 81 is inserted into the reception opening 900 such that the bottom walls 803, 813 of the chamber elements 80, 81 face the first tilted face 904 and are in contact with the coupling pads 920, 930. At the same time, the chamber elements 80, 81 with the flat faces 806, 816 abut the second tilted face 903 such that the flat face 806 of the first chamber element 80 faces the infrared window 940 and the flat face 816 of the second chamber element 81 faces the infrared window 950.

For inserting the measurement device 8 into the reception opening 900, the closure element 91 may be opened, as it is shown in FIGS. 10 and 11. After inserting the measurement device 8 into the reception opening 900, the closure element 91 is closed, as shown in FIG. 9, such that a front edge of the closure element 91 comes to lie at an edge section 901 of the base 90. In the closed position the closure element 91 via a locking element 914 is locked with respect to the base 90 in that the locking element 914 engages a corresponding locking element 902 of the base 90 such that a positive locking between the closure element 91 and the base 90 is achieved.

In the closed position of the closure element 91 fixing elements 912, 913 protruding from the inner face of the closure element 91 facing the inside of the reception opening 900 abut the chamber elements 80, 81 at their top walls 805, 815. By means of the fixing elements 912, 913 a force is exerted on the chamber elements 80, 81 along the longitudinal axis L such that the chamber elements 80, 81 are pressed with a predefined force against the coupling pads 920, 930 of the ultrasonic sensor elements 92, 93. In this way, a beneficial coupling of the sensor elements 92, 93 to the bottom walls 803, 813 of the chamber elements 80, 81 is achieved.

Figure 13:
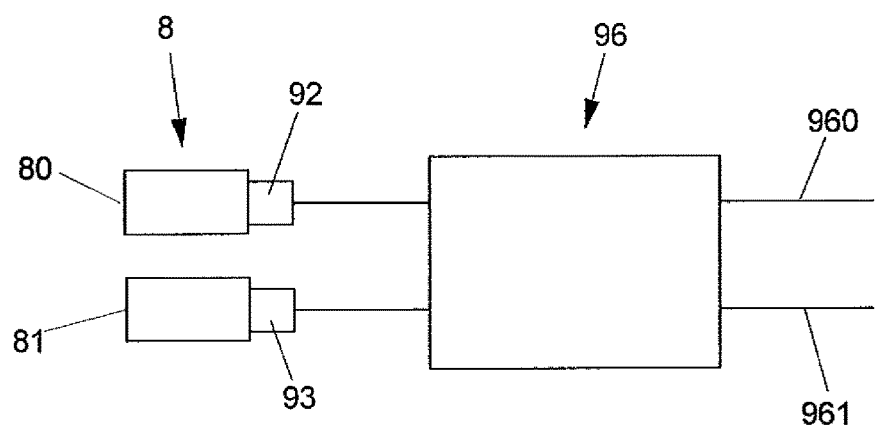
FIG. 13 shows a schematic view of a control circuit connected to ultrasonic sensor elements of the holder device.

As shown in FIGS. 9 and 10, connecting lines 921, 931 are connected to the sensor elements 92, 93 and serve to electrically connect the sensor elements 92, 93 to a control unit 96, as it is shown in FIG. 13. Via the connecting lines 921, 931 the senor elements 92, 93 are excited to produce ultrasonic pulses P, and reflection signals received at the sensor elements 92, 93 are transmitted as sensor signals to the control unit 96.

In the control unit 96 a signal processing takes place in order to determine a haematocrit value of the blood flowing through the respective chamber element 80, 81. The control unit 96 comprises a power line 960 for electrically feeding the control unit 96 and a data output line 961 for providing data to other units.

The infrared sensor elements 94, 95 are used to determine a temperature of blood in the chamber elements 80, 81. As sown in FIG. 12, each infrared sensor element 94, 95 may be connected to a connecting line 941 (shown in FIG. 12 only for the infrared sensor element 94) for transmitting sensor signals to the control unit 96.

As shown in FIG. 12, the chamber elements 80, 81 with their longitudinal axes L are arranged at an angle α with respect to the direction of gravity G. Because the outlet port 801, 811 for each chamber element 80, 81 is arranged at the top wall 805, 815 of the respective chamber element 80, 81, air bubbles within the flow chamber 802, 812 may rise in the flow chamber 802, 812 and may be washed out through the respective outlet port 801, 811 such that the air bubbles are removed from the flow chamber 802, 812. Hence, measurements within the chamber element 80, 81 are not disturbed by the presence of air bubbles.

The outlet port 801, 811 for each chamber element 80, 81, when inserted into the holder device 9, herein beneficially is arranged at the highest point of the flow chamber 802, 812 with respect to the direction of gravity G, as it is illustrated in FIG. 12. This ensures that air bubbles rising in the flow chamber 802, 812 against the direction of gravity G may exit the flow chamber 802, 812 through the outlet port 801, 811 and are not caught within the flow chamber 802, 812.

The closure element 91 comprises an opening 911 through which the handle 84 extends when the measurement device 8 is inserted into the reception opening 900 and the closure element 91 is closed, as it is shown in FIG. 9. A user hence may hold the measurement device 8 by grabbing the handle 84 until the closure element 91 is fully closed, which makes it easy to insert the measurement device 8 in a correct manner into the holder device 9.

The holder device 9 beneficially is constituted such that the measurement device 8 may be inserted into the reception opening 900 only in a single position. This ensures that the measurement device 8 is inserted correctly into the holder device 9 even by untrained users.

The idea underlying the invention is not limited to the embodiments described above, but may be used also in entirely different embodiments.

In particular, the invention is not limited to autotransfusion systems, but may be used also within other medical systems for processing blood.

LIST OF REFERENCE NUMERALS

1 Blood processing apparatus
10 Housing
100 Lid
101 Control panel
11 Stand
12 Base
120 Wheels
2 Reservoir container
20-22 Tube section
3 Re-transfusion bag
30-32 Tube section
4 Bag for washing solution
40, 41 Tube section
5 Waste bag
50 Connection tube
6 Pump bed
60-62 Tube segment
600-620 Pump mechanism
7 Washing chamber
70 Connector
71 Conduit
72 Connector
8 Measurement device
80, 81 Chamber element
800, 810 Inlet port
801, 811 Outlet port
802, 812 Flow chamber
803, 813 Bottom wall
804, 814 Circumferential wall
805, 815 Top wall
806, 816 Flat face
807, 817 Conduit
808, 818 Conduit
809, 819 Inner surface
84 Handle
85 Housing
850, 851 Housing part
86 Webs
9 Holder device
90 Base
900 Reception opening
901 Edge section
902 Locking element
903, 904 Tilted face
91 Closure element
910 Pivoting axis
911 Opening
912, 913 Fixing element
914 Locking element
92, 93 Ultrasonic sensor element
920, 930 Coupling pad
921, 931 Connecting line
94, 95 Infrared sensor element
940, 950 Infrared window
941, 951 Connection
96 Control unit
960, 961 Connections
α Angle B Wall thickness
D Rotational axis
E1-E5 Face
F Flow
F1-F4 Flow direction
G Direction of gravity
H Height
L Longitudinal axis
P Pulse
R Rotational movement
T1, T2 Tangential axis
W Width

The invention claimed is:

1. A blood processing apparatus, comprising:
a measurement device having a first chamber element for measuring a haematocrit value of a blood fluid, the first chamber element comprising a first inlet port connectable to a first reservoir container for allowing a flow from the first reservoir container into the first chamber element and a first outlet port for allowing a flow out of the first chamber element, and a second chamber element comprising a second inlet port for allowing a flow into the second chamber element and a second outlet port connectable to a second reservoir container for allowing a flow out of the second chamber element towards the second reservoir container,
a first pump mechanism for pumping a blood fluid in a flow direction from the first reservoir container towards the blood processing apparatus, and
a second pump mechanism for pumping a blood fluid in a flow direction from the blood processing apparatus towards the second reservoir container,
wherein the first pump mechanism is located upstream of the first inlet port of the first chamber element and the second pump mechanism is located upstream of the second inlet port of the second chamber element.

2. The blood processing apparatus according to claim 1, further comprising a holder device for holding the measurement device, the holder device comprising a base having a reception opening for receiving the measurement device and a closure element movably arranged on the base for locking the measurement device in an inserted position in the reception opening.

3. The blood processing apparatus according to claim 2, wherein the holder device comprises a first ultrasonic sensor element which in the inserted position of the measurement device faces the first chamber element and a second ultrasonic sensor element which in the inserted position of the measurement device faces the second chamber element.

4. The blood processing apparatus according to claim 3, wherein the holder device comprises a first infrared sensor element which in the inserted position of the measurement device faces the first chamber element and a second infrared sensor element which in the inserted position of the measurement device faces the second chamber element.

5. The blood processing apparatus according to claim 4, wherein the base comprises a first tilted face and a second tilted face extending transversely with respect to the first tilted face, wherein the first and the second ultrasonic sensor element are arranged on the first tilted face and the first and the second infrared sensor element are arranged on the second tilted face.

6. The blood processing apparatus according to claim 1, wherein the first outlet port of the first chamber element is connected to a washing chamber of the blood processing apparatus for allowing a flow into the washing chamber.

7. The blood processing apparatus according to claim 6, wherein the second inlet port of the second chamber element is connected to the washing chamber for receiving a flow from the washing chamber.

8. The blood processing apparatus according to claim 1, wherein the first pump mechanism and the second pump mechanism are adapted to act on tube segments of a tubing set.

9. The blood processing apparatus according to claim 1, wherein the measurement device is part of a disposable tubing set.

10. The blood processing apparatus according to claim 1, wherein the first and the second chamber elements each extend along a longitudinal axis and comprise a circumferential wall extending about the longitudinal axis and encompassing a flow chamber, wherein the first and the second chamber elements extend with their longitudinal axes in parallel to each other.

11. The blood processing apparatus according to claim 1, wherein the first and the second chamber elements are integrally connected to each other via webs extending in between the chamber elements.

* * * * *